(12) United States Patent
Rutz (10) Patent No.: US 11,413,268 B2
(45) Date of Patent: *Aug. 16, 2022

(54) CPC DISTRIBUTION CHROMATOGRAPHY OF CANNABINOIDS

(71) Applicant: Spectrum Therapeutics GmbH, Neumarkt (DE)

(72) Inventor: Andreas Rutz, Dornhausen (DE)

(73) Assignee: SPECTRUM THERAPEUTICS GMBH

(*) Notice: Subject to any disclaimer, the term of this patent is extended or adjusted under 35 U.S.C. 154(b) by 0 days.

This patent is subject to a terminal disclaimer.

(21) Appl. No.: 16/740,863

(22) Filed: Jan. 13, 2020

(65) Prior Publication Data
US 2020/0147034 A1 May 14, 2020

Related U.S. Application Data

(63) Continuation of application No. 15/552,331, filed as application No. PCT/EP2016/054250 on Feb. 29, 2016, now Pat. No. 10,568,863.

(30) Foreign Application Priority Data

Feb. 27, 2015 (EP) ..................................... 15156901

(51) Int. Cl.
| | | |
|---|---|---|
| *A61K 31/352* | (2006.01) | |
| *B01D 15/18* | (2006.01) | |
| *B01D 15/30* | (2006.01) | |
| *C07D 311/80* | (2006.01) | |
| *G01N 30/38* | (2006.01) | |

(52) U.S. Cl.
CPC ........ *A61K 31/352* (2013.01); *B01D 15/1892* (2013.01); *B01D 15/30* (2013.01); *C07D 311/80* (2013.01); *G01N 30/38* (2013.01); *G01N 2030/381* (2013.01)

(58) Field of Classification Search
CPC .. A61K 31/352; B01D 15/18; B01D 15/1892; B01D 15/30; C07D 311/80; G01N 30/38; G01N 2030/381
See application file for complete search history.

(56) References Cited

U.S. PATENT DOCUMENTS

| | | | |
|---|---|---|---|
| 8,324,408 B2 | 12/2012 | Erler et al. | |
| 8,895,078 B2 | 11/2014 | Mueller | |
| 2010/0179098 A1 | 7/2010 | Lee | |
| 2010/0210860 A1 | 8/2010 | Erler et al. | |
| 2013/0216488 A1* | 8/2013 | Hernandez-Brenes | A23L 3/3499 424/59 |

(Continued)

FOREIGN PATENT DOCUMENTS

| | | |
|---|---|---|
| DE | 10051427 | 6/2002 |
| DE | 102005028937 | 1/2007 |
| WO | WO 02/32420 | 4/2002 |

OTHER PUBLICATIONS

"Class 2 residual solvents," ALS Environmental, accessed Jun. 25, 2019, 2 pages.

(Continued)

*Primary Examiner* — Benjamin L Lebron
(74) *Attorney, Agent, or Firm* — Sheridan Ross P.C.

(57) ABSTRACT

The invention relates to cannabinoids and their isolation and purification and to obtaining them by means of centrifugal partition chromatography.

6 Claims, 9 Drawing Sheets

(56) References Cited

U.S. PATENT DOCUMENTS

2014/0243405 A1 8/2014 Whalley et al.
2018/0036278 A1 2/2018 Rutz

OTHER PUBLICATIONS

"Tert-Buty Methyl Ether," Sigma-Aldrich, Inc., accessed Jun. 25, 2019, 4 pages.
Hazekamp et al., "Preparative Isolation of Cannabinoids from *Cannabis sativa* by Centrifugal Partition Chromatography," Journal of Liquid Chromatography & Related Technologies, vol. 27, No. 15, 2004, pp. 2421-2439.
Hazekamp, "Cannabis; extracting the medicine," Leiden University Doctoral Thesis, Sep. 5, 2007, 187 pages.
Hopmann et al., "A priori selection of the mobile and stationary purse in centrigual partition chromatography and counter-current chromatography," Journal of Chromatography A, vol. 1238, 2012, pp. 68-76.
Yin et al., "Trends in Counter-Current Chromatography: Applications to Natural Products Purification," Separation & Purification Reviews, vol. 39, No. 1-2, 2010, pp. 33-62.
International Search Report and Written Opinion for International (PCT) Patent Application No. PCT/EP2016/054250, dated Jun. 13, 2016, 13 pages.

\* cited by examiner

CPC DISTRIBUTION CHROMATOGRAPHY OF CANNABINOIDS

CROSS-REFERENCE TO RELATED APPLICATIONS

This application is a continuation of U.S. patent application Ser. No. 15/552,331 filed Aug. 21, 2017, which is a national stage application under 35 U.S.C. § 371 and claims the benefit of PCT Application No. PCT/EP2016/054250 having an international filing date of Feb. 29, 2016, which designated the United States, which PCT application claimed the benefit of European Patent Application Serial Number 15156901.9, filed on Feb. 27, 2015, the entire disclosures of each of which are incorporated herein by reference.

DESCRIPTION

The invention relates to cannabinoids and to the isolation and purification thereof, as well as to obtaining cannabinoids by means of Centrifugal Partition Chromatography (CPC).

CPC is used for obtaining and enriching plant content substances from botanical extracts on the analytical, semi-preparative, and preparative scale. CPC is a liquid-liquid chromatography method that uses a generally two-phase solvent system.

It permits nearly loss-free separation of highly complex mixtures of substances from crude extracts. Manufacturers of such centrifugal partition chromatographs for performing CPC are e.g. Kromaton S.a.r.l (Annonay, FR) and Armen Instrument Sas (Saint-Avé, FR).

Compared to high-performance liquid chromatography (HPLC), CPC is simpler and also more cost-effective, since there are no matrix effects or irreversible adsorptions on the solid phases.

A 2-phase solvent mixture is used in the CPC method, as in prevalent liquid-liquid chromatography methods such as for instance high speed countercurrent chromatography (HSCCC). The upper or the lower phase may be selected to be used as the stationary phase. However, in contrast to HSCCC, CPC does not use a capillary coil, but instead works with a rotor provided with several hundred separation chambers. The substances contained in the botanical extract are separated between the mobile and stationary phase in these chambers, which are inserted directly behind one another.

During the separation process, the system is caused to rotate rapidly (up to 2,500 rpm). Because of this, firstly, depending on the flow direction, the desired phase is retained in the rotor of the CPC, and, secondly, the separation of the two phases is accelerated due to the centrifugal force. This makes it possible to use greater flow speeds and consequently enables the throughput of large quantities of substances in a short period of time so that this separation technology has preparative application.

The separation coefficient K of the desired substance between the two phases should be in the range between 0.7 and 4.5. If K is lower, the substance elutes too rapidly, so that no separation can take place. If K is higher, the retention time for rapid purification of large quantities of a botanical extract becomes too long.

The prior art describes that cannabinoids may be obtained from cannabis extract by means of $CO_2$ extraction (DE10051427C1). Nevertheless, the cannabinoids, such as e.g. THC (A, dronabinol) and CBD (B, cannabidiol) are not obtained with absolute purity.

Figure 1:
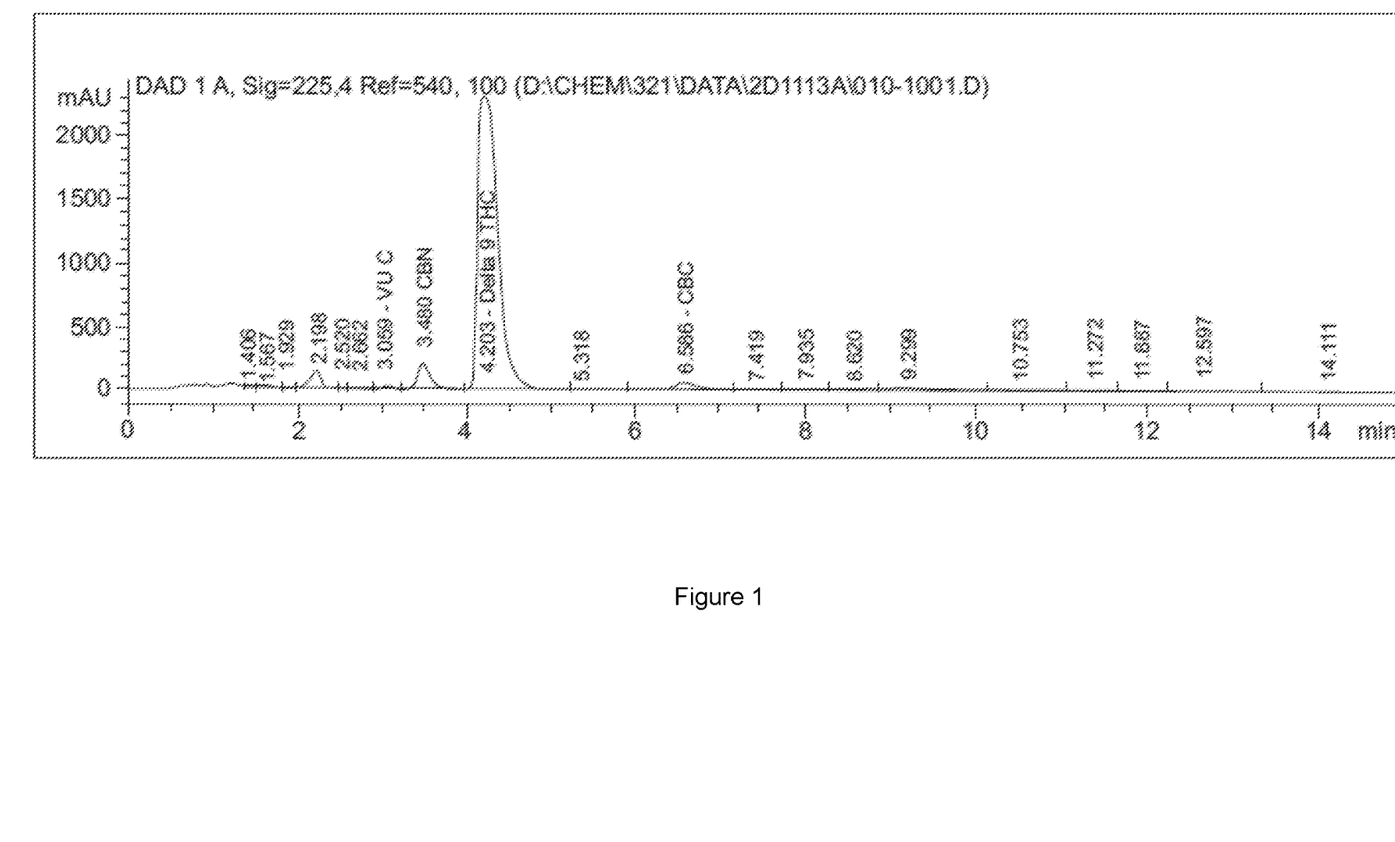
Figure 2:
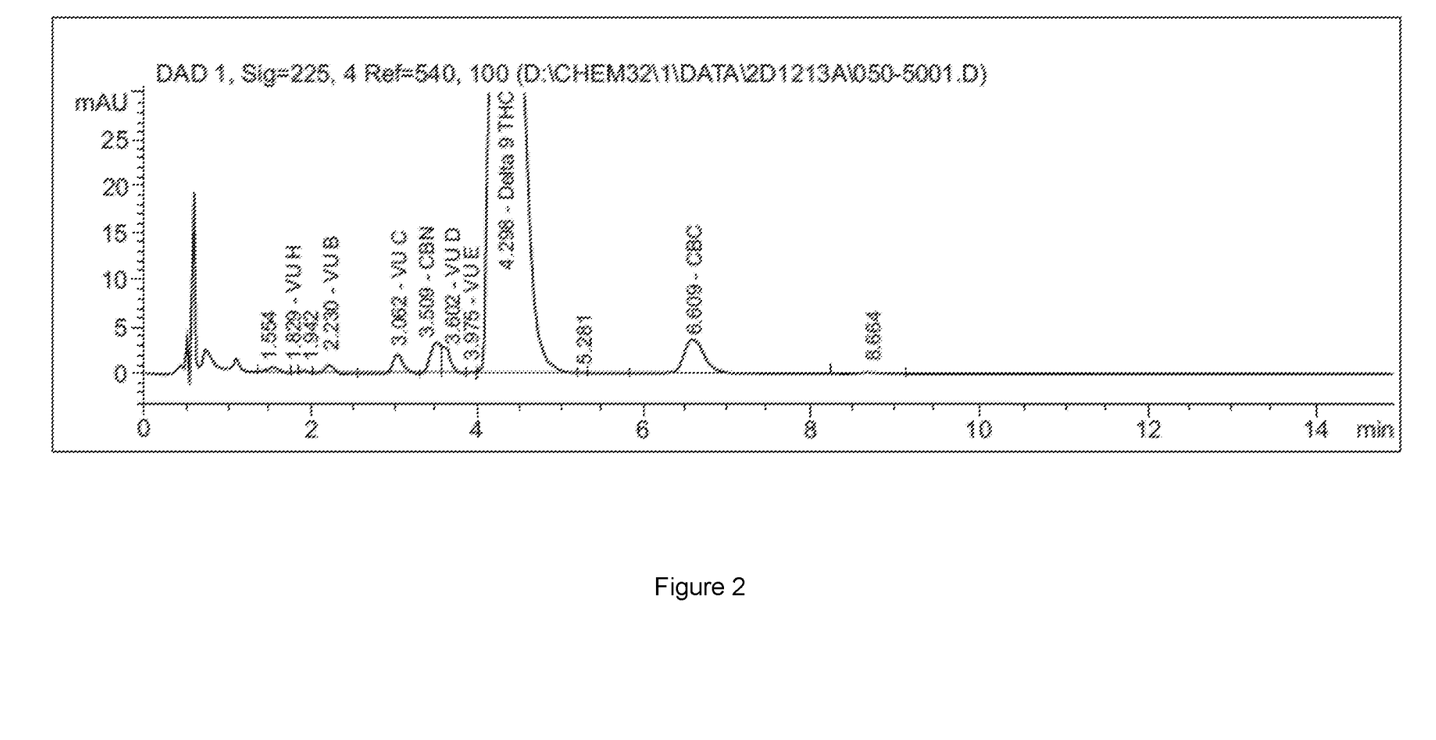
Figure 3:
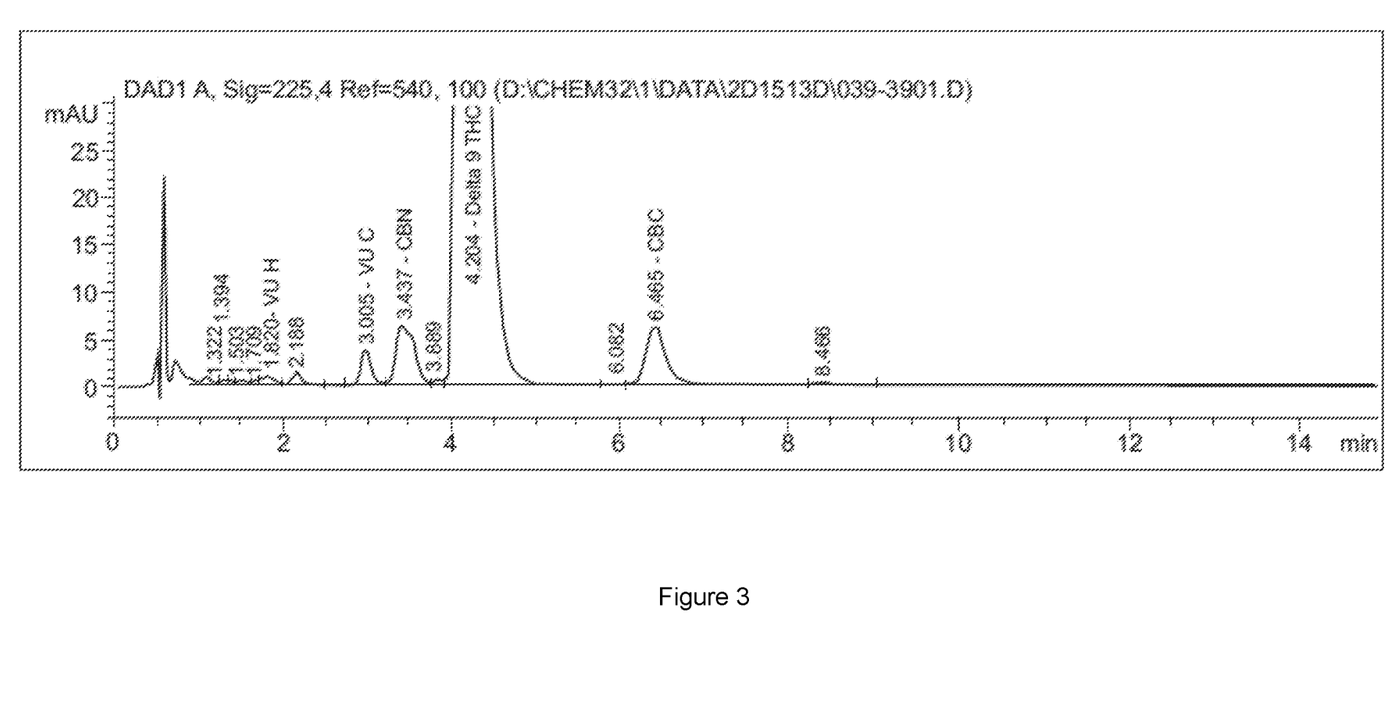
Figure 4:
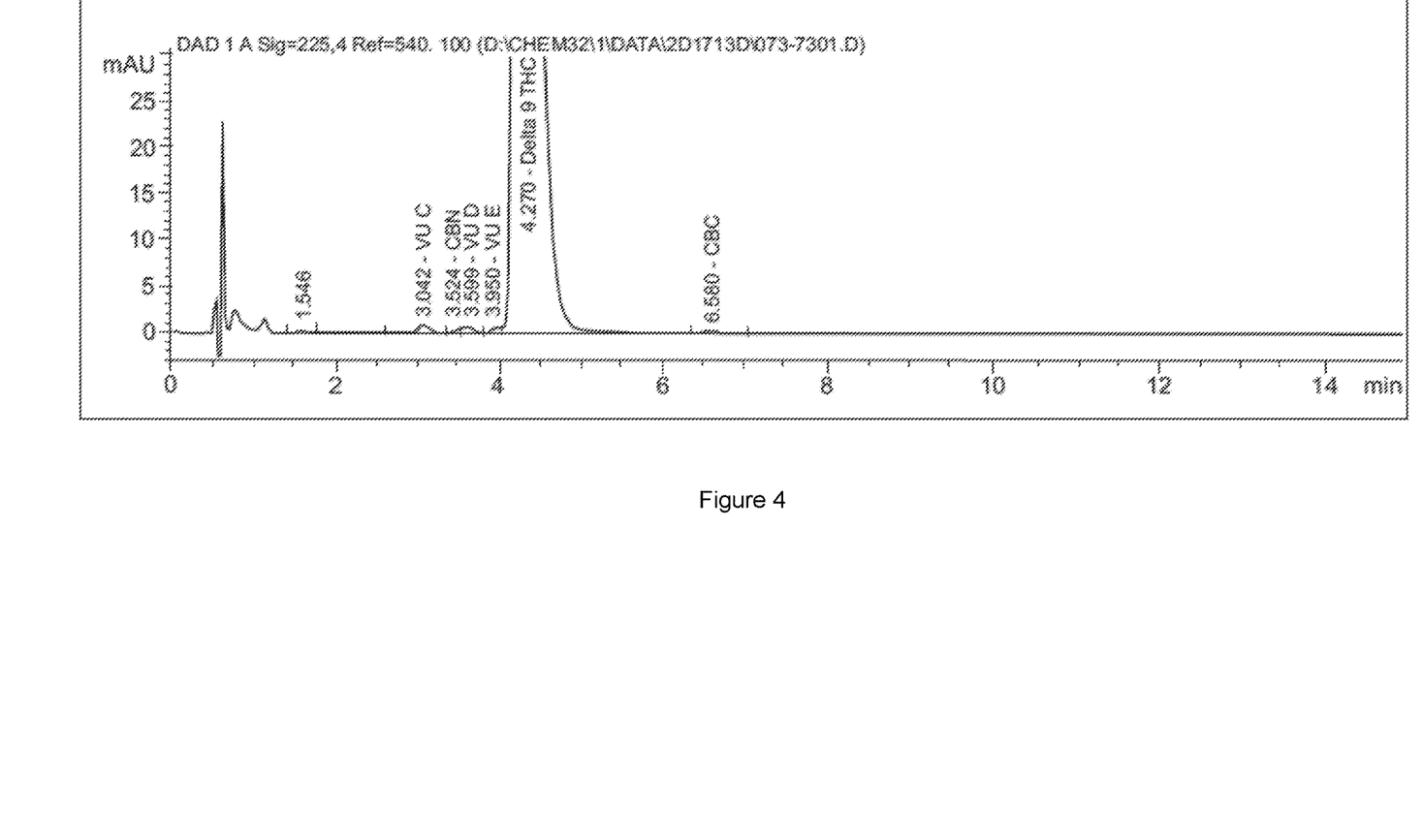
Figure 5:
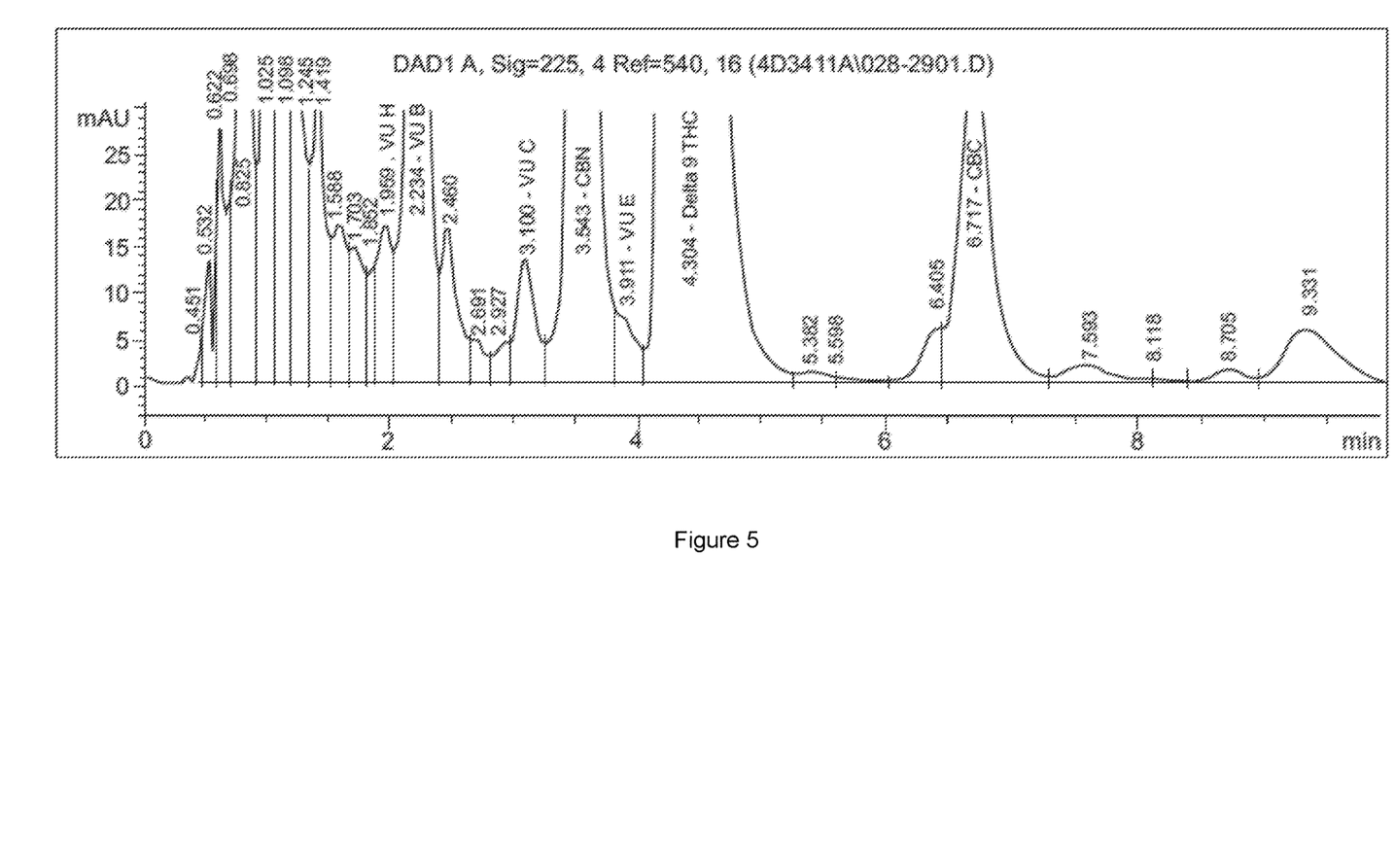
Figure 6:
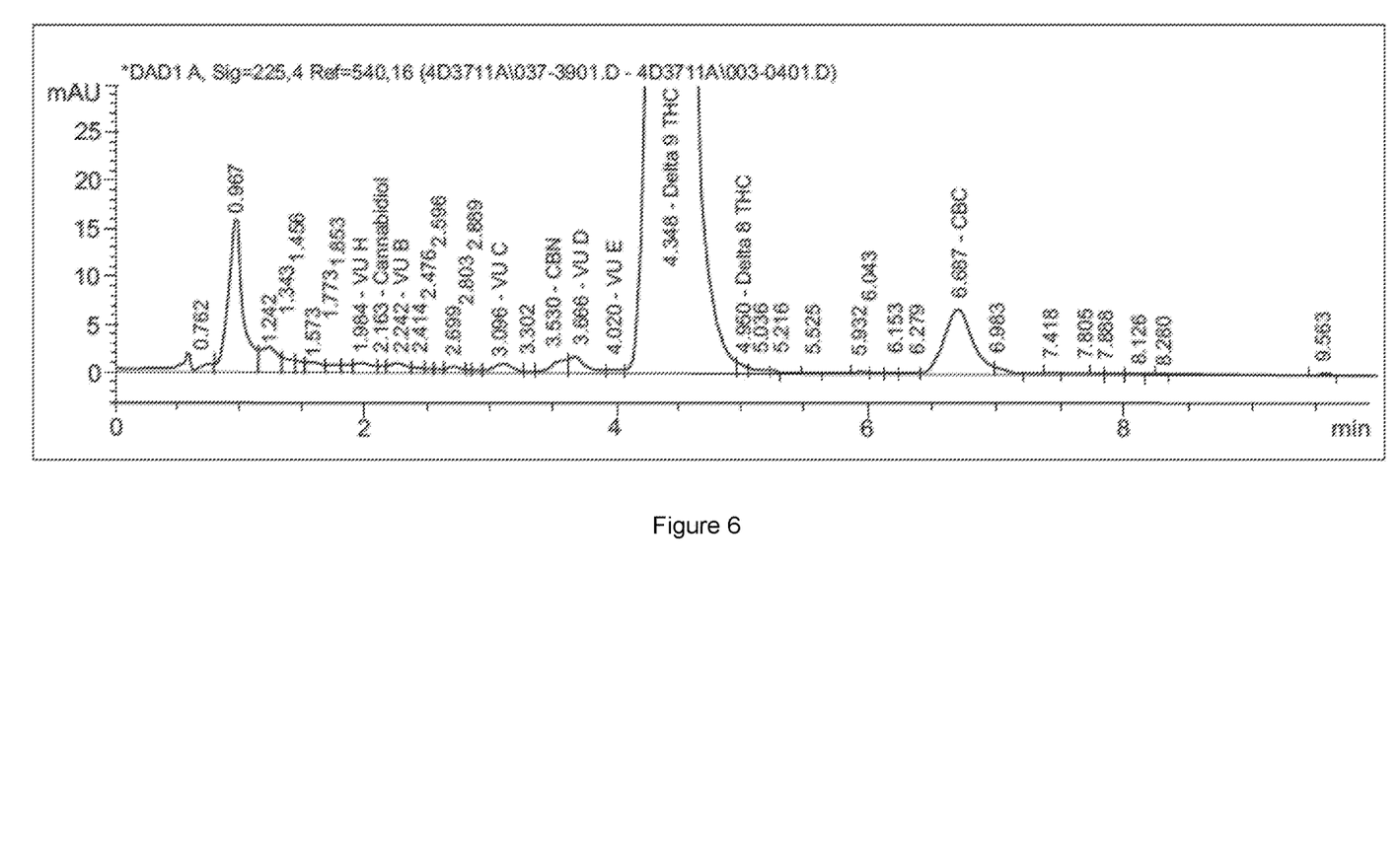
Figure 7:
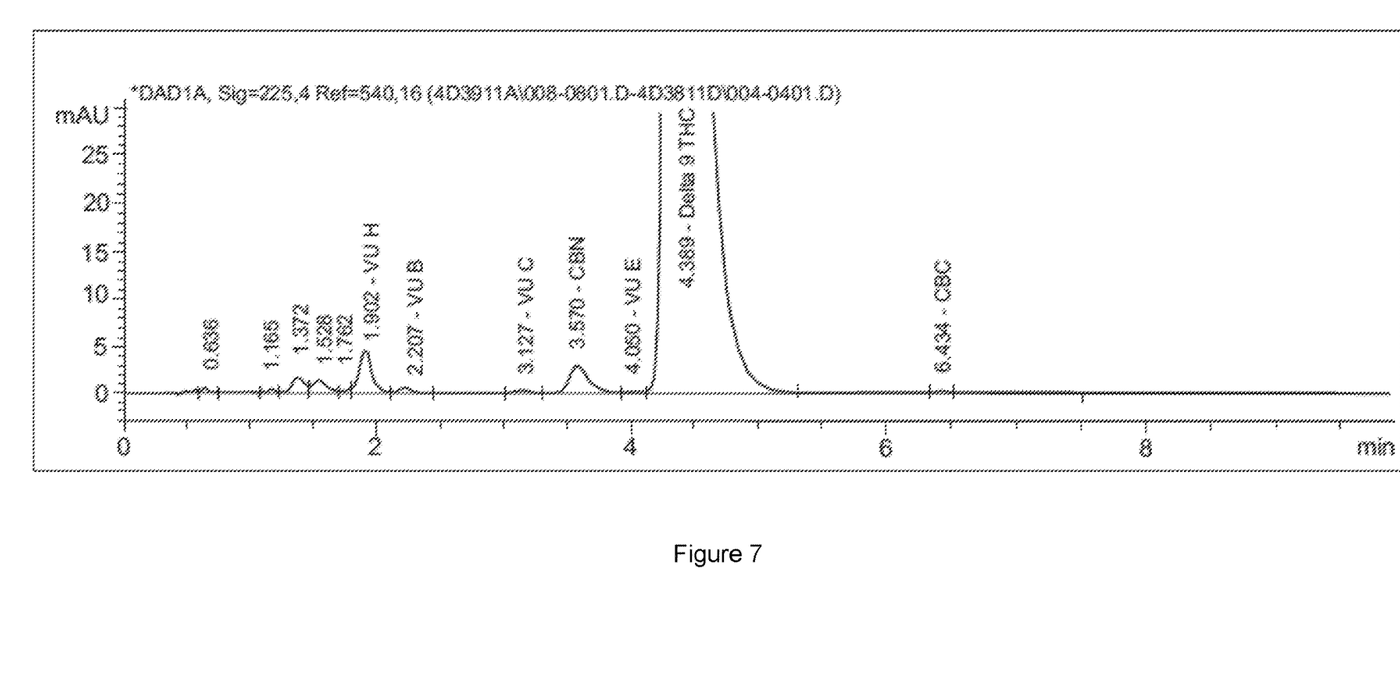

FIG. 1: Dronabinol (A) ((6aR-trans)-6a,7,8,10a-tetrahydro-6,6,9-trimethyl-3-pentyl-6H-dibenzo[b,d]pyran-1-ol, $\Delta^9$-tetrahydrocannabinol ($\Delta^9$THC)), cannabidiol (CBD) (B) ((2-[1R-3-methyl-6-(1-methylethenyl]-2-cyclohexen-1-yl]-5-pentyl-1,3-benzenediol))

Chromatographic separation and preparative purification of cannabinoids—in particular obtaining cannabinoids, preferably $\Delta^9$THC and CBD, having a high degree of purity of greater than 95%—still represents a challenge.

In the prior art, Hazekamp, A., 2007, Doctoral thesis, Leiden University, and Arno Hazekamp, Ruud Simons, Anja Peltenburg-Looman, Melvin Sengers, Rianne van Zweden, Robert Verpoorte, Preparative isolation of cannabinoids from *Cannabis sativa* by centrifugal partition chromatography, J. Liq. Chrom. Rel. Technol. 2004, 27(15): 2421-2439, describe the preparative obtaining of cannabinoids by means of CPC. However, in the prior art a two-phase system based on hexane is used and the maximum purity attained is 93.1%. In addition, low yields are attained. Furthermore, hexane is a neurotoxin of solvent class 2 (ICH Guidelines).

The object is therefore to provide an improved method for separating and/or purifying cannabinoids from cannabis botanical extracts, which method eliminates at least some of these drawbacks and in particular is able to provide preparatively, in many applications, a higher yield and purity of cannabinoids, especially CBD and/or THC.

This object is attained using a method according to one of the patent claims.

Accordingly, a method for separating and/or purifying cannabinoids is provided that includes at least one liquid-liquid centrifugal partition chromatography step or the use of a centrifugal partition chromatograph for liquid-liquid centrifugal partition chromatography for separating and/or purifying cannabinoids, wherein a solvent made of cyclohexane, heptane, n-heptane, iso-heptane, octane, n-octane, iso-octane is selected and is kept stationary by centrifugal force and a second, non-miscible liquid phase may be pumped through as the mobile phase. According to the invention, n-heptane is preferred, however.

The density and the viscosity of cyclohexane, n-heptane, iso-octane are greater than the density/viscosity of n-hexane, so that, e.g., compared to the second mobile phase such as e.g. acetonitrile, a more stable two-phase system is produced, so that better retention of the stationary phase is possible and consequently greater separation is attained, so that, compared to n-hexane, higher purity and yield are always attained—with a purity of greater than 95%, even 99%.

The inventive method and/or the inventive use advantageously demonstrate lower eluent consumption in addition to no deposits on a stationary phase, so that it is not necessary to regenerate the stationary phase or to prepare or remove interfering components. Product recovery is nearly quantitative, since stationary and mobile phases may simply be exchanged. In addition, the stationary phase is completely renewed during each run and may be purified or renewed in a simple manner using distillation. The purity of the isolated cannabinoids is often so high that no additional chromatographic purification steps are needed. It is also simple to execute the method on the industrial scale. The yield of cannabinoids is often sharply higher compared to the prior art, as shall be explained in greater detail in the following. The number of process stages required may generally be significantly reduced compared to alternative techniques. It is particularly advantageous that cannabinoids may be obtained from any desired cannabis plants or their extracts. This includes cannabis extracts from cannabis plants (*Cannabis sativa, Cannabis indica, Cannabis ruderalis*), such as hemp, industrial hemp, pharmaceutical hemp, fiber hemp, etc.

According to the invention, provided for cannabinoids is the advantageous use of the two solvents acetonitrile and heptane, which are not miscible with one another, at a flow of 50 to 600 mL per min, preferably at a flow of 200 to 300 mL per min., during the separation, and max. flow during rinsing, at a speed of 50 to 1,500 rpm, preferably at a speed of 900 to 1,100 rpm during the separation. Furthermore preferred is the use of the upper phase as the stationary phase.

In another preferred embodiment, t-butyl methyl ether (TBME) may be added to the solvent, specifically 1 to 15% (v/v), preferably 9 to 13% (v/v).

The second non-miscible liquid phase may also include solvents such as methanol, ethyl acetate, or water, to which 1-15% t-butyl methyl ether (TBME) may be added, as well.

Examples according to the invention of solvent systems include, but are not limited to (stationary phase/mobile phase):

n-heptane/acetonitrile 1:1 (without t-butyl methyl ether),
n-heptane/ethylacetate/acetonitrile,
n-heptane/ethylacetate/t-butyl methyl ether/acetonitrile,
n-heptane/ethylacetate/methanol/water,
n-heptane/methanol/water,
n-heptane/ethanol/water,
n-heptane/acetone/water,
n-heptane/methanol/acetonitrile,
n-heptane/ethanol/acetonitrile,
n-heptane/acetone/acetonitrile,
n-heptane/chloroform/acetonitrile,
n-heptane/chloroform/methanol,
n-heptane/methanol,
n-heptane/ethanol/methanol,
n-heptane/n-butanol/acetonitrile,
n-heptane/2-propanol/water,
n-heptane/n-propanol/water,
n-heptane/2-propanol/acetonitrile,
n-heptane/n-propanol/acetonitrile,
n-heptane/dichloromethane/acetonitrile,
n-heptane/dichloromethane/methanol,
n-heptane/tetrahydrofuran/acetonitrile,
n-heptane/benzotrifluoride/acetonitrile,
Cyclohexane/methanol/water,
Cyclohexane/methanol/acetonitrile,
Cyclohexane/t-butyl methyl ether/water,
Cyclohexane/acetonitrile/water,
Isooctane/methanol,
Isooctane/methanol/water,
Isooctane/ethyl acetate/methanol/water.

However, according to the invention, acetonitrile, possibly with 1-15% t-butyl methyl ether (TBME) added, is particularly advantageous.

It may furthermore be provided that the inventive method is performed one or a plurality of times (see e.g. Example 1).

The selection of these solvents permits cannabinoids, preferably $\Delta^9$THC and CBD to be obtained with a high degree of purity of greater than 95%.

Therefore the invention relates to a cannabis extract that may be or is obtained according to the inventive method, wherein the dronabinol purity is greater than 95%, and especially is 99.6%.

Therefore the invention relates to a cannabis extract that may be or is obtained according to the inventive method, wherein the cannabidiol (CBD) purity is greater than 95%, and especially is 99.3%.

When using a 12,500 mL CPC rotor, it is also advantageously possible to purify up to 100 g extract per run.

Advantageously, only 120 to 160 min. are needed per separation, including preparation and rinse times. The fractions containing cannabinoids are released by the organic solvents. After concentrating in a vacuum, extracts are obtained that have a desired cannabinoid content of up to 70-99% by mass, preferably greater than 95% by mass.

In the context of this invention, especially the following substances shall be understood to be cannabinoids:

Cannabigerol-type (CBG): Cannabigerol ((E)-CBG-$C_5$), cannabigerol monomethyl ether ((E)-CBGM-$C_5$ A), cannabinerolic acid A ((Z)-CBGA-$C_5$ A), cannabigerovarin ((E)-CBGV-$C_3$), cannabigerolic acid A ((E)-CBGA-$C_5$ A), cannabigerolic acid A monomethyl ether ((E)-CBGAM-$C_5$ A), Cannabigerovaric acid A ((E)-CBGVA-$C_3$ A);

Cannabichromene-type (CBC): Cannabichromene (CBC-$C_5$), cannabichromene acid A (CBCA-$C_5$ A), cannabichromevarin (CBCV-$C_3$), cannabichromevarinic acid A (CBCVA-C3 A);

Cannabidiol-type(CBD): Cannabidiol (CBD-$C_5$), cannabidiol monomethyl ether (CBDM-$C_5$), cannabidiol-C4 (CBD-$C_4$), cannabidivarin (CBDV-$C_3$), cannabidiorcol (CBD-$C_1$), cannabidiolic acid (CBDA-$C_5$), cannabidivarinic acid (CBDVA-$C_3$);

Cannabinodiol-type(CBND): Cannabinodiol (CBND-$C_5$), cannabinodivarin (CBND-$C_3$);

Tetrahydrocannabinol-type (THC): $\Delta$9-tetrahydrocannabinol ($\Delta$9-THC-$C_5$), $\Delta$9-tetrahydrocannabinol-C4 ($\Delta$9-THC-$C_4$), $\Delta$9-tetrahydrocannabivarin ($\Delta$9-THCV-$C_3$), $\Delta$9-tetrahydrocannabiorcol ($\Delta$9-THCO-$C_1$), $\Delta$9-tetrahydrocannabinolic acid ($\Delta$9-THCA-$C_5$ A), $\Delta$9-tetrahydrocannabinolic acid B ($\Delta$9-THCA-$C_5$ B), $\Delta$9-tetrahydrocannabinolic acid-C4 ($\Delta$9-THCA-$C_4$ A and/or B), $\Delta$9-tetrahydrocannabivarinic acid A ($\Delta$9-THCVA-$C_3$ A), $\Delta$9-tetrahydrocannabiorcolic acid($\Delta$9-THCOA-$C_1$ A and/or B), (−)-$\Delta$8-trans-(6aR,10aR)-$\Delta$8-tetrahydrocannabinol ($\Delta$8-THC-$C_5$), (−)-$\Delta$8-trans-(6aR,10aR)-tetrahydrocannabinolic acid A ($\Delta$8-THCA-$C_5$ A); (−)-(6aS,10aR)-$\Delta$9-tetrahydrocannabinol ((−)-cis-$\Delta$9-THC-$C_5$);

Cannabinol-type(CBN): Cannabinol CBN-$C_5$, cannabinol-C4 (CBN-$C_4$), cannabivarin (CBN-$C_3$), cannabinol-C2 (CBN-$C_2$), cannabiorcol (CBN-$C_1$), cannabinolic acid A (CBNA-$C_5$ A), cannabinol methylether (CBNM-$C_5$)

Cannabitriol-type (CBT): (−)-(9R,10R)-trans-cannabitriol ((−)-trans-CBT-$C_5$), (+)-(9S,10S)-cannabitriol ((+)-trans-CBT-$C_5$), (±))-(9R,10S/9S, 10R)-cannabitriol ((±)-cis-CBT-$C_5$), (−)-(9R,10R)-trans[10-O-ethyl-cannabitriol] ((−)-trans-CBT-OEt-$C_5$), (+)-(9R,10R/9S,10S)-cannabitriol-$C_3$ ((+)-trans-CBT-$C_3$),8,9-dihydroxy-Δ6a(10a) tetrahydrocannabinol (8,9-Di-OH-CBT-$C_5$), cannabidiolic acid A (CBDA-$C_5$ 9-OH-CBT-C5 ester), (−)-(6aR,9S,10S,10aR)-9,10-dihydroxy-hexahydrocannabinol, cannabiripsol cannabiripsol-C5, (−)-6a,7,10a-trihydroxy-Δ9-tetrahydrocannabinol ((−)-cannabitetrol), 10-oxo-Δ6a(10a) tetrahydrocannabinol (OTHC);

Cannabielsoin-type (CBE): (5aS,6S, 9R, 9aR)-$C_5$-cannabielsoin (CBE-$C_5$), (5aS,6S, 9R, 9aR)-$C_3$-cannabielsoin (CBE-$C_3$), (5aS,6S,9R,9aR)-cannabielsoic acid A (CBEA-$C_5$ A), (5aS,6S,9R,9aR)-cannabielsoic acid B (CBEA-$C_5$ B), (5aS,6S,9R,9aR)-C3-cannabielsoic acid B (CBEA-$C_3$ B), cannabiglendol-C3 (OH-iso-HHCV-$C_3$), dehydrocannabifuran (DCBF-$C_5$), cannabifuran (CBF-$C_5$);

Isocannabinoids: (−)-Δ7-trans-(1R,3R,6R)-isotetrahydrocannabinol, (±)-Δ7-1,2-cis-(1R,3R,6S/1S,3S,6R)-isotetrahydrocannabivarin, (−)-7-trans-(1R,3R, 6R)-isotetrahydrocannabivarin;

Cannabicyclol-type (CBL): (±)-(1aS,3aR,8bR, 8cR)-cannabicyclol (CBL-$C_5$), (±)-(1aS,3aR,8bR,8cR)-cannabicyclolic acid A (CBLA-$C_5$ A), (±)-(1aS,3aR,8bR,8cR)-cannabicyclovarin (CBLV-$C_3$);

Cannabicitran-type (CBT): Cannabicitran (CBT-$C_5$);

Cannabichromanone-type (CBCN): Cannabichromanone (CBCN-$C_5$), cannabichromanone-C3 (CBCN-$C_3$), cannabicoumaronone (CBCON-$C_5$).

Cannabidiol (CBD-$C_5$) and Δ9-tetrahydrocannabinol (Δ9-THC-$C_5$) are particularly preferred, however.

In the context of the present invention, the term "liquid-liquid centrifugal partition chromatography step" shall be construed especially to mean chromatography which proceeds as follows:

A specific quantity of a substance mixture is conducted, with a liquid mobile phase, through a phase that is kept stationary, wherein the latter is kept stationary using centrifugal force. In another preferred embodiment, the liquid-liquid centrifugal partition chromatography may be performed continuously. To this end, the two phases are conducted in the counter-current and continuous separation occurs, instead of a temporally offset (discontinuous) output (see, e.g., Yin, Lianhong; Li, Yingnan; Lu, Binan; Jia, Yujie; Peng, Jinyong, Trends in Counter-Current Chromatography: Applications to Natural Products Purification Separation and Purification Reviews (2010), 39(1-2), 33-62).

Corresponding to its interactions with the stationary phase, which interactions differ in strength, the substances exit continuously or discontinuously and may be separated. However, while the stationary phase in liquid chromatography comprises a packed solid bed in a column, in liquid-liquid centrifugal partition chromatography there is a second, non-miscible liquid phase that is kept stationary by suitable devices, such as e.g. a rotor, using centrifugal force, in particular by means of a corresponding centrifugal partition chromatograph (see above).

"Cannabis extract" in the context of this invention means any processed extract from a cannabis plant or hemp plant that includes cannabinoids. The extract may be a primary extract or may be a partly processed extract. The manufacture of cannabis extracts is adequately described in the prior art. Suitable cannabis plants or (fiber) hemp plants are those such as pharmaceutical hemp or fiber hemp.

In another preferred embodiment, at least one preparative column (solid phase, such as e.g. silica gel) may be upstream or downstream (Example 2).

EXAMPLE AND FIGURES

These examples and figures are intended solely for explaining the invention, without limiting the invention to these examples.

Example 1: Cannabinoids from Hemp

Figure 8:
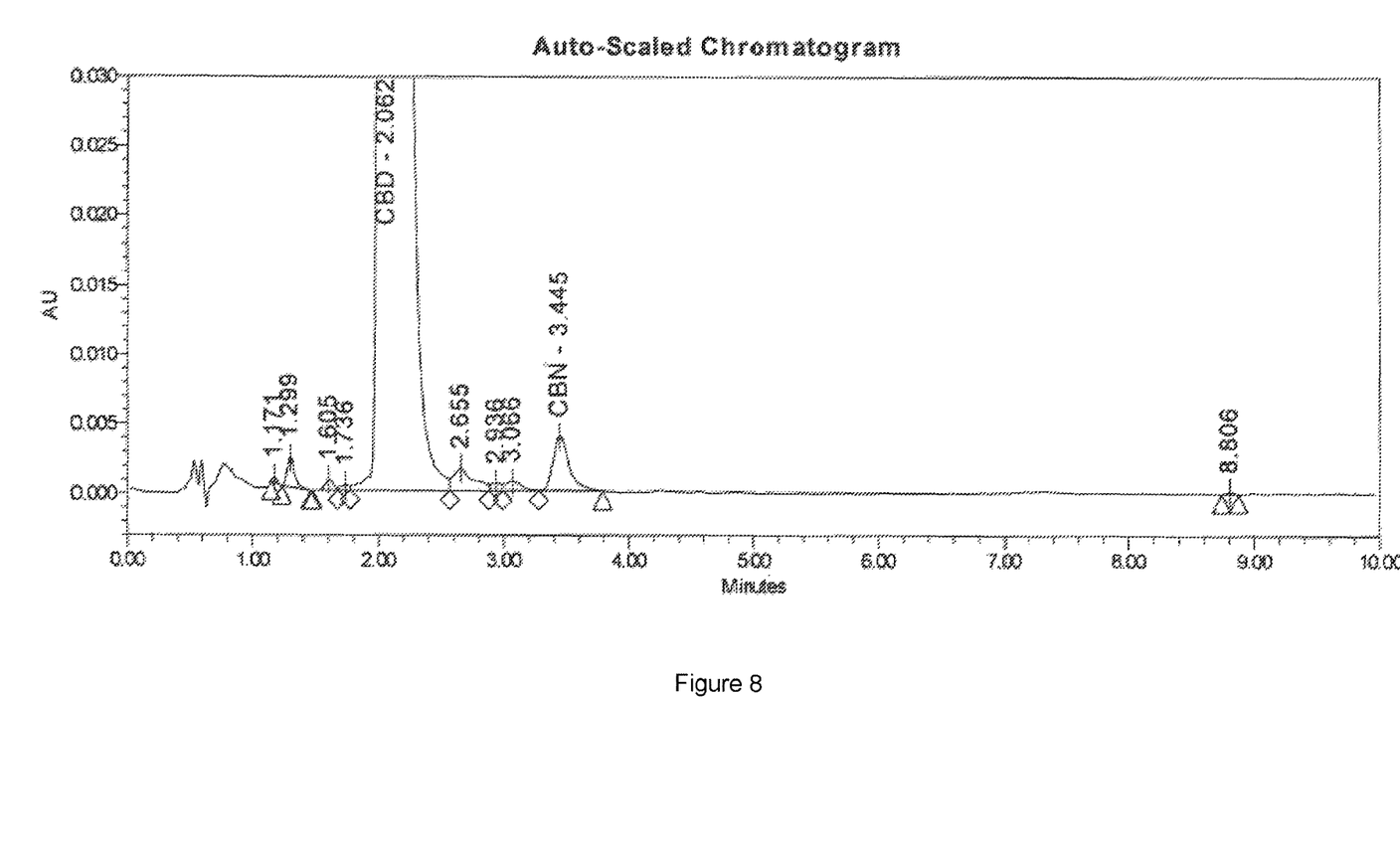
Figure 9:
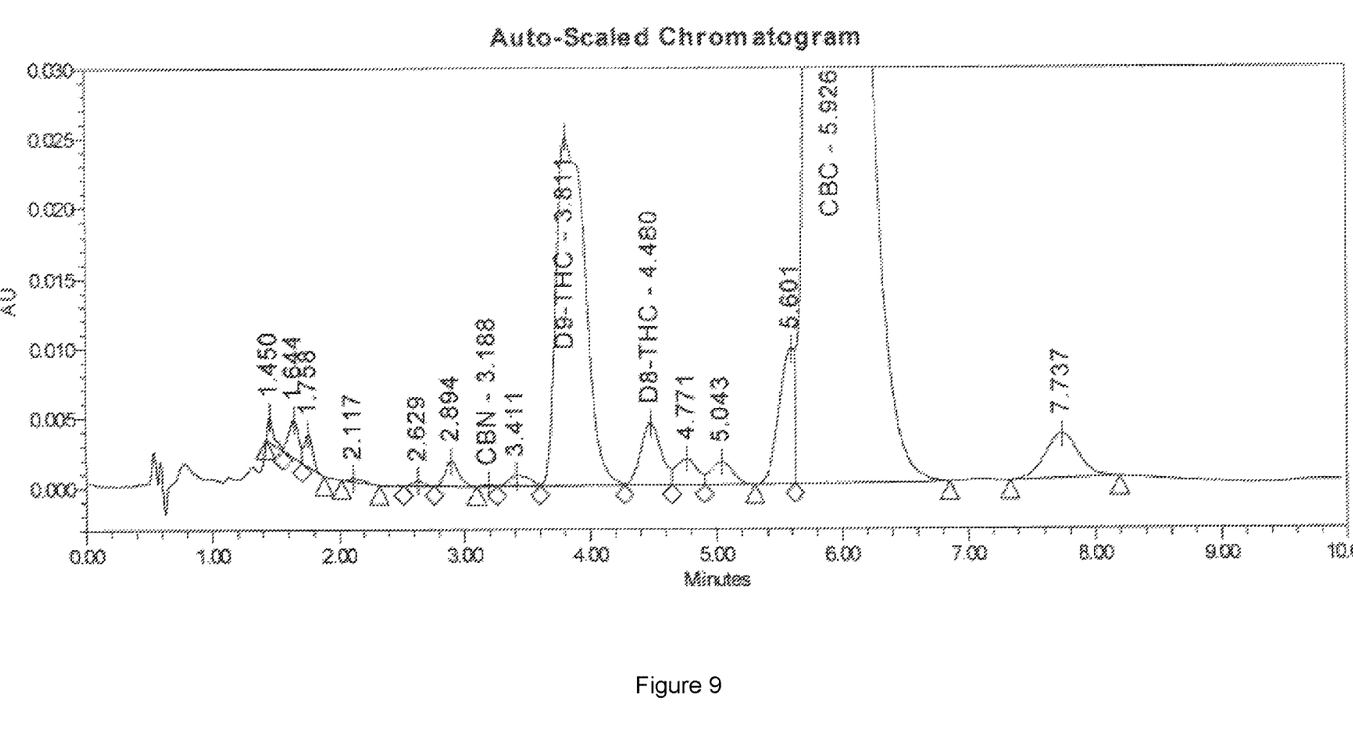

Recovery of THC (dronabinol) (FIGS. 1-7), CBD (FIG. 8), or CBC (FIG. 9) from pharmaceutical hemp or industrial/fiber hemp: extraction of cannabis flos by means of heptane, decarboxylation at 120° C. in a vacuum, dissolution in heptane, purification in CPC.

1. CPC

1st run: Quantitative separation of CBN, proportional separation of CBC:

Mobile phase: Acetonitrile TBME approx. 12%
Stationary phase: heptane TBME approx. 10%
From dronabinol 84.1% with approx. 15.9% impurities, wherein 5.4% is CBN and 2.2% is CBC.
Color: Dark brown to black.
FIG. 1
Result:
Dronabinol 97.7% with approx. 2.3% impurities, wherein 0.4% is CBN and 0.9% is CBC.
Color: Yellow
FIG. 2
Optional $2^{nd}$ run: Quantitative purification of CBC
Mobile phase: acetonitrile TBME approx. 12%
Stationary phase: heptane TBME approx. 10%
From dronabinol 97.7% with approx. 2.3% impurities, wherein 0.8% is CBN and 0.9% is CBC.
Color: Yellow
FIG. 3
Result:
Dronabinol 99.6% with approx. 0.4% impurities, wherein 0.04% is CBN and 0.05% is CBC.
Color: Yellowish (additional brightening)
FIG. 4

Example 2: CPC with Subsequent Run Through Silica Gel Column

Run: Quantitative separation of CBN
No separation of CBC
Mobile phase: acetonitrile, purum
Stationary phase: heptane, purum
From dronabinol 81% with approx. 19% impurities, wherein 4.2% is CBN and 1.6% is CBC.
Color blackish to dark brown
FIG. 5
Result:
Dronabinol 94.5% with approx. 5.5% impurities, wherein 0.16% is CBN and 1.4% is CBC.
Color: Yellow
FIG. 6
Then preparative chromatography using silica gel for quantitative separation of CBC:
Mobile phase heptane 3% TBME
From dronabinol 96.4% with approx. 3.6% impurities, wherein 0.36% is CBN and 1.8% is CBC.

Color: Yellow
FIG. 7
Result:
Dronabinol 98.6% with approx. 1.4% impurities, wherein 0.4% is CBN and 0.0% is CBC.
Color: Colorless
FIG. 8:
Result:
Cannabidiol 99.3% with approx. 0.7% impurities, wherein 0.3% is CBN.
Color: Colorless, crystallizable
FIG. 9
Result:
Cannabichromene 94.1% with approx. 5.9% impurities, wherein dronabinol is 3.39% and Δ8-THC is 0.19%.

The invention claimed is:

1. A method for separating and/or purifying cannabinoids from a cannabis extract, the method including at least one liquid-liquid centrifugal partition chromatography step comprising a first solvent phase and a second non-miscible liquid phase, wherein the first solvent phase is heptane and is kept stationary by centrifugal force and the second non-miscible liquid phase is methanol, and wherein 1% to 15% (v/v) t-butyl methyl ether is added to the first solvent phase and/or the second non-miscible liquid phase.

2. The method for separating and/or purifying cannabinoids from a cannabis extract according to claim 1, wherein the first solvent phase is n-heptane.

3. The method for separating and/or purifying cannabinoids from a cannabis extract according to claim 1, having a flow of 50 mL to 600 mL per minute and/or a speed of 50 rpm to 1,500 rpm.

4. The method for separating and/or purifying cannabinoids from a cannabis extract according to claim 1, wherein the first solvent phase and the second non-miscible liquid phase are conducted in the counter current and continuous separation occurs.

5. The method for separating and/or purifying cannabinoids from a cannabis extract according to claim 1, wherein at least one preparative column is upstream or downstream.

6. The method for separating and/or purifying cannabinoids from a cannabis extract according to claim 1, wherein 9% to 13% (v/v) t-butyl methyl ether is added to the first solvent phase and/or the second non-miscible liquid phase.

\* \* \* \* \*